United States Patent [19]

Inoue et al.

[11] Patent Number: 5,549,739
[45] Date of Patent: Aug. 27, 1996

[54] WOOD MODIFIER COMPOSITION

[75] Inventors: Tadashi Inoue, 13-4-102, Hiyoshidai 2-chome, Hukuyama-shi, Japan; Tetsuzo Tsujimura, Shibayama-machi, Japan

[73] Assignees: Nippon Suisan Kaisha, Ltd., Tokyo; Kyowa Tecnos Co., Ltd., Chiba; Tadashi Inoue, Hiroshima, all of Japan

[21] Appl. No.: 486,583

[22] Filed: Jun. 7, 1995

Related U.S. Application Data

[63] Continuation-in-part of Ser. No. 347,130, Nov. 23, 1994, abandoned.

[30] Foreign Application Priority Data

Nov. 26, 1993 [JP] Japan ................................. 5-340318

[51] Int. Cl.$^6$ .................................................. A01N 33/00
[52] U.S. Cl. ..................... 106/15.05; 106/18.12; 106/18.3; 106/18.32; 106/287.34; 106/162.2; 424/724; 427/297; 427/440; 514/55
[58] Field of Search .............................. 106/15.05, 18.32, 106/287.34, 217, 18.12, 18.13, 18.3; 427/297, 440; 424/618, 629, 638, 650, 651, 653, 657, 659, 724; 514/55

[56] References Cited

U.S. PATENT DOCUMENTS 5,348,799  9/1994  Boston ........................... 428/323

FOREIGN PATENT DOCUMENTS

| | | |
|---|---|---|
| 63-189859 | 8/1988 | Japan . |
| 3-38081 | 6/1991 | Japan . |
| 4-249151 | 9/1992 | Japan . |
| 6-170810 | 6/1994 | Japan . |

*Primary Examiner*—Anthony Green
*Attorney, Agent, or Firm*—Sughrue, Mion, Zinn, Macpeak & Seas

[57] ABSTRACT

A wood modifier composition containing a mixture of a water-soluble, low molecular weight chitosan substance and colloidal silica is disclosed. The mixture contains from about 15 to about 300 parts by weight of $SiO_2$ per part of the low molecular weight chitosan substance, and may also contain one or more compounds capable of improving wood quality, selected from boron, copper, silver, aluminum, titanium, manganese and black lead. The wood modifier composition is preferably used as an aqueous solution having a pH of about 5 to about 12. The wood modifier composition according to the present invention can be used as a neutral aqueous solution having a low viscosity which can easily penetrate into wood cells and be safely fixed therein. Impregnation of wood materials by colloidal silica can be easily achieved by the wood modifier composition according to the present invention, thereby improving defects in natural wood materials and strengthening the physical properties of wood by providing wood preservation, fire retardance, shrinkage resistance, etc. without lessening the desirable characteristics of the wood materials.

20 Claims, 4 Drawing Sheets

FIG. 4 and cockWOOD MODIFIER COMPOSITION

This is a continuation-in-part of application Ser. No. 08/347,130 filed Nov. 23, 1994, abandoned.

FIELD OF THE INVENTION

This invention relates to a wood modifier composition, more particularly, it relates to a wood modifier composition comprising a mixture of a water-soluble low molecular weight substance of chitosan which is, for example, a chemically decomposed product or an enzymatically decomposed product of chitosan, and colloidal silica.

More specifically, the present invention relates to a wood modifier composition which is nontoxic to living body, and which reinforces physical properties of woods, improves resistance to fire, and provides improved shrinkage resistance, antibacterial and antifungal properties, high impregnation property, maintenance of superior processing characteristics, resistance to light and moisture replacement.

BACKGROUND OF THE INVENTION

A natural material, wood, generally requires modification of its characteristics such as putrefaction, dimensional instability and inflammability depending upon its utility. For example, antibacterial, antifungal and insecticidal treatments of wood by using a preservation agent is generally achieved by providing the wood with water repellency by adding paraffin, a surface active agent, etc. to the preservation agent. Also, gas oil, light oil, a high boiling point kerosin fraction and the like are used as preservative solvents to improve the penetrating property. Since these solvents have high boiling points, however, the treated wood becomes hard to dry. Components in these treating compositions must necessarily be safe to human as well as under working conditions.

Hitherto, impregnation of wood with inorganic substances has been considered, but the most important problem in such an impregnation is a low impregnated amount in wood. It is technically difficult to introduce the inorganic substances into an inner vessel portion of the center of wood by impregnation. When the wood is forcedly impregnated, the inorganic substances tend to be leaked out and are thus difficult to be fixed in the wood. Further, such a forced impregnation causes discoloration of wood, thereby reducing its commercial value, and also may cause decoloration of coating materials applied on the surface of the impregnated wood. When sodium silicate is used for impregnation, parenchyma tend to be deteriorated due to a strong alkalinity of sodium silicate. In addition, the wood treating agents must be selected so as not to discharge strongly toxic gases and/or heavy metals when the treated woods are disposed as scrap wood after passing its durable years.

Woods are basically limited natural resource and become usable materials after growth for a long period of term, and hence reinforcement and improvement of the functions of the woods are problems which have conventionally been desired to be solved. Accordingly, a wood modifier composition which is practically useful for providing the wood with functions such as non-putrefaction, fire-resistance, dimension stability, non-attack by harmful insects is strongly desired while retaining decomposability in the ground.

SUMMARY OF THE INVENTION

An object of the present invention is to provide a practically useful wood modifier composition which is capable of providing woods with various functions such as non-putrefaction, fire-resistance, dimension stability, non-attack by harmful insects (arthropods such as white ants and cockroach), resistance against basidiomycetes and wood deteriorating microorganisms, and which is expected to provide the treated wood with a natural disintegration property and to return a silicon component contained in the wood modifier composition to a natural soil component when the treated wood is crushed and buried in the ground as waste disposals after passing its durable years.

According to the present invention, the above-described object can be achieved by a wood modifier composition comprising a mixture of a water-soluble low molecular weight substance of chitosan, such as a chemically decomposed product or an enzymatically decomposed product of chitosan (hereinafter sometimes referred to as a water-soluble chitosan or low molecular weight chitosan), and colloidal silica.

The wood modifier composition according to the present invention can be used as a neutral aqueous solution having a low viscosity which is easily penetrating into cytoplasm of the wood material and is safely fixed in the cytoplasm. It has been reported that impregnation of wood cells with silicic acid in an amount of 5% or more is effective for modification of wood materials, and such an inorganization of wood materials by colloidal silica can be easily achieved by the wood modifier composition according to the present invention, thereby improving defects of the natural wood materials and strengthening physical properties such as a preservative effect, a fire retardant property, a shrinkage resistant property, etc. without deteriorating the desirable nature of the wood materials.

DETAILED DESCRIPTION OF THE INVENTION

The wood modifier composition according to the present invention comprises a mixture of a water-soluble low molecular weight substance of chitosan, such as a chemically or enzymatically decomposed product of chitosan, and colloidal silica.

As a means for reinforcing the functional strength of woods, the wood is generally impregnated with a resin and the like, but the resistance to fire of the woods can not be improved by the resin impregnation. One of the means for solving the problem of fire resistance of woods is inorganization of wood, and the present invention solves the problem by impregnating the wood with colloidal silica in admixture with a water-soluble low molecular weight substance of chitosan, or by impregnating the wood with a composite aqueous solution of the above mixture and compounds capable of improving wood quality added thereto.

The wood is composed of starch, cellulose, hemicellulose, pectin, and trace amounts of organometal compounds of copper, manganese and iron. Putrefaction of woods are caused by putrefying microorganisms, white ants or the like which decompose starch, cellulose, hemicellulose, pectin and the like constituents of the wood with cellulase, pectinase, formic acid and the like for assimilation. On the other hand, in cell walls and proteoglycan of the putrefying microorganisms, white ants, fungi, and arthropods, a chitonous substance is present as a constituting material.

The water-soluble low molecular weight substance of chitosan having a molecular weight in the range of from 320 to 48,000 are heterosaccharides composed of cationic polysaccharides and oligosaccharides having an isoelectric point at about pH 8.5, and have affinity to woods. This affinity is considered attributed to the similarity in molecular structures that cellulose has a hydroxyl group bonded to the ethyl group at the C-5 position and a hydroxyl group at the C-3 position, and, on the other hand, chitosan also has a hydroxyl group at the C-5 position, a hydroxyl group at the C-3 position and a positively charged amino group at the C-2 position which is a reactive cation. In addition, the water-soluble low molecular weight substance of chitosan obtained by chemical decomposition, contains 2,5-anhydromannose having an aldehyde group at the terminal of the molecular chain is present, and hence the substance appears to have stability in the inside of woods.

It has been reported that the low molecular weight chitosan consisting of about seven D-glucosamines has an antibacterial activity and the low molecular weight chitosan having a molecular weight of 48,000 or less has an antifungal activity.

The wood treated with chitosan was examined for antifungal activity against filamentous fungus, *Coriolus versicolor, Gyrophana lacrymans* and *Polyporus versisporus* by observation with scanning electron microscope. As a result, the microscopic observation revealed that, when these microorganisms decompose chitosan with enzymes that they secrete and enter the wood, their hyphae and glycans having a chitonous substance as a structural material were decomposed by the action of the above mentioned enzymes, and hence it is considered that the growth capacity of these microorganisms is inhibited.

Colloidal silica is a silicon dioxide suspended in water in the form of hydrate, and is a dispersion in which amorphous silica particles are independently and stably dispersed in a liquid dispersing medium. The amorphous silicon particles are formed by polymerization of water glass or silicic acid obtained by, for example, hydrolysis of silicates or silicon halides, followed by growing into a particle size of colloids.

Colloidal silica can be used at a proportion of from 15 to 300 parts, preferably 50 to 150 parts, by weight of $SiO_2$ per part by weight of a chemically or enzymatically decomposed product of chitosan. For example, one thousand ml of colloidal silica having a $SiO_2$ content of 30% contains 300 g of $SiO_2$, which corresponds to 50 parts by weight per part by weight of the chitosan decomposed product and one thousand ml of colloidal silica having a $SiO_2$ content of 40% contains 400 g of $SiO_2$, which corresponds to about 67 parts by weight per part by weight of the chitosan decomposed product.

The composition according to the present invention may further contain one or more compounds capable of improving wood quality, such as metal compounds, semi-metal compounds, boron, calcium and carbon. These compounds are not particularly limited provided that they penetrate into wood materials and function therein. These compounds are preferably boron, copper, silver, iron, aluminum, manganese, chromium, titanium, calcium and graphite, with copper, silver, titanium and boric acid being more preferred. The compound may be in the form of a salt, oxide or chloride such as titanium oxide, aluminum chloride, aluminum oxide, chromium oxide or potassium chromate. Boron can be used as boric acid, calcium borate, borax or borosilicate. These compounds function to improve wood quality, for example, as follows. Boric acid has antifungal and insecticidal activities. Copper and silver have antiputrefactive and antifungal activities. Titanium and chromium prevent deterioration of wood materials by ultraviolet. Carbon (graphite) strengthens wood materials. Iron oxide is a metal pigment for coloring wood materials. These compounds are used in an amount effective for exerting their activities in wood materials.

The composition according to the present invention is used as an aqueous solution having a pH of from 5 to 12, preferably from 6 to 10. When boric acid is added to the mixture, the mixture can be used stably in a neutral state.

The low molecular weight chitosan can be prepared by a known method including enzymatic decomposition as described in Sakai et al, *Journal of the Japanese Society of Starch Science*, 37.:79–86 (1990), and chemical decomposition as described in Zehavi et al, *Biochem. Preparation*, 13:14 (1971), Yaku et al, *Cellulo. Chem. Technol.*, 11:421 (1977), JP-A-2-22301, JP-A-2-11601 and JP-A-54-148890 (the term "JP-A" used herein means an unexamined published Japanese patent application). The enzymatically decomposed product of chitosan has a molecular weight of about 320 to about 48,000, and the chemically decomposed product of chitosan is a mixture of a low molecular weight product of chitosan having a molecular weight of about 320 to about 48,000 and 2,5-anhydromannose. These chitosan components can be used as an aqueous solution having a pH of 8.5 or in a powder state, and are preferably used at a concentration of from 0.01 to about 5% by weight in an aqueous solution.

To the aqueous solution of the low molecular weight chitosan and/or 2,5-anhydromannose adjusted as described above is added, for example, colloidal silica having a pH of 9.9 while stirring at a temperature in the range of from about 0° C. to about 90° C. to immediately form a stable solution. When boric acid is added thereto, the resulting solution becomes neutral and stable. An excess amount of boric acid should not be mixed with the solution though the addition of an excess amount of boric acid does not cause precipitation of silicon. This suggests that the low molecular weight substance of chitosan functions as masking the surface of silicon molecules, thereby reducing a particle size of silicon.

It appears that the low molecular weight chitosan and 2,5-anhydromannose are capable of specifically introducing the bonded or complexed inorganic substances into cell tissues of woods.

A high molecular weight substance of chitosan precipitates and sediments in the solution and are removed from the solution by, for example, centrifugation since these high molecular weight substances are difficult to use for impregnating and introducing into parenchyma cells and cell walls, cell membranes, vessel portions, and vascular bundles.

The impregnation of the wood modifier composition of the present invention into wood can be performed by floating the wood in the solution or coating the solution on the surface of the wood by, for example, a spray-coating method, then subjecting the resulting wood to a vacuum impregnation treatment, a pressurized impregnation treatment, the diffusion impregnation method or the secondary diffusion impregnation method, and then dried by evaporation. The evaporation drying may be conducted by impregnating the treated wood into alcohols, phenols or petroleum materials to evaporate water contained in the wood with taking advantage of azeotropic property. By performing the evaporation drying, the water-soluble low molecular weight substance of chitosan and colloidal silica can be precipitated and fixed in the cells of wood.

The water-soluble low molecular weight substance of chitosan functions as an introducing agent and enhances to impregnate in the cells of wood colloidal silica, metal and/or semimetal compounds or ions of these compounds and iron or iron compounds such as iron oxide which is used as a dye. The materials which are conventionally used for impregnation such as resins can also be introduced into the cells of wood using the composition of the present invention.

Colloidal silica has excellent properties in the fire retardance, the reinforcement of physical functions and the preservation effect. It is easily presumed that colloidal silica forms a complex with the hydroxyl groups at the C-5 position and at the C-3 position of the saccharide which is a component of the water-soluble low molecular weight substance of chitosan. The saccharides of the low molecular weight substance of chitosan bond to organic materials such as nucleic acids, bases, various glycoproteins, glycolipids, hormon proteins, antibodies, alkaloids and lectins to function for physiological adjustment, manifestation and control. It is considered that these heterosaccharides bond to cellulose, hemicellulose and pectin in parenchyma constituting the wood and fixed in the vessel portions as well as the central portions of wood. On the other hand, the crystal structure of silicic acid in the wood appears to be different from the structure conventionally reported, and silicic acid is crystallized in such a state that the low molecular weight substance of chitosan is present between silicic acid molecules.

The present invention will now be further illustrated by the following examples, but the present invention should not be limited thereto. Unless otherwise specified, "%" used in the following Examples means "wt. %".

EXAMPLE 1

To 20 g of chitosan (1% viscosity, 12 cps) was added 180 ml of water. The resulting solution was heated up to 50° C. in a water bath under stirring (150 rpm) and 13.7 g of 35% hydrogen peroxide and 4 g of acetic acid were added thereto. In this instance, hydrogen peroxide was added in an amount of 24.0% based on the weight of chitosan. The reaction was carried out at 50° C. for 18 hours under stirring.

The reaction mixture was adjusted to pH 10 with sodium hydroxide and allowed to stand at 5° C. for 18 hours. Then, the mixture was centrifuged at 2,000 rpm for 15 minutes and the resulting supernatant was subjected to desalting with an electric dialysis apparatus. After the dialysis thus obtained was concentrated to 20 ml using an evaporator, the concentrate was added dropwise to 400 ml of acetone. The precipitate was collected by filtration using Toyo Roshi No. 2 filter paper and dried to obtain 10.6 g of pale yellow water-soluble chitosan.

The decomposed product of chitosan thus obtained was subjected to gel filtration by HPLC under the following conditions:

Column, Asahipak GS-320;
Mobile phase, 0.2 M acetic acid, 0.2 M sodium acetate;
Flow rate, 0.6 ml/min;
Column temperature, 55° C.;
Detector, differential refractometer (Toso RI-8);
Molecular weight marker, pullulan;
HPLC apparatus, Toso HLC-803D; and
Recorder, SIC chromatocorder 11 (GPC cartridge 030538-V1).

As a result, it was found that the decomposed product of chitosan had number average molecular weight of 5,084, weight average molecular weight of 5,602 and the degree of dispersion of 1.10.

A solution containing 5 wt. % of the above-obtained low molecular weight chitosan and having a pH of about 8.5 in 1,000 ml of pure water was prepared, and 120 ml of the resulting aqueous solution was added to 1,000 ml of colloidal silica (Snowtex C produced by Nissan Chemical Co., Ltd., pure $SiO_2$ content, 30.4%; pure $Na_{2O}$ content, 0.42 ppm; pH 9.9; viscosity, 5.8 cp), followed by stirring for 30 minutes.

Then, to the resulting mixed solution of colloidal silica and the low molecular weight chitosan was added 90 g of boric acid (pure $BO_2$ content, 99.5%; powder form, pH 4) in small portions with stirring while paying attention so as not to cause gelation by boric acid on the surface of the solution. In this case, boric acid was mixed with the mixed solution of colloidal silica and the low molecular weight substance of chitosan while repeating a sol-gel formation.

A stable mixing proportion of these components was achieved at a neutral pH, but at this point a part of boric acid added still remained undissolved in the solution and existed therein in a dispersoid.

Further, the resulting mixture was stirred for about 12 hours at constant room temperature. Since evaporation of a part of the bound water of colloidal silica and the low molecular weight substance of chitosan occurred during this time, the evaporation of the bound water was prevented appropriately to obtain a substantially transparent solution which was lightly brown and which had a stable viscosity of about 6 cp. If the activity of the low molecular weight substance of chitosan is lost, the resulting solution becomes a white turbid viscous solution which is difficult to use for impregnation of wood.

Alternatively, substantially the same result was obtained by adding 6 g of a low molecular weight chitosan in place of the aqueous solution of the low molecular weight substance of chitosan used above to 1,000 ml of colloidal silica, Cataloid S (produced by Shokubai Kagaku Co., Ltd., a pure $SiO_2$ content, 30.4%; a pure $Na_2O$ content, 0.42 ppm; pH 9.9; viscosity, 5.8 cp).

EXAMPLE 2

Snowtex C having different colloidal silica concentrations (products of Nissan Chemical Co., Ltd.) and Cataloid S (produced by Shokubai Kagaku Co., Ltd., pure silicon content of 20%; pH 9.5) were used to determine possible mixing proportions of the low molecular weight substance of chitosan and boric acid. As a result, the possible mixing proportions of boric acid were found to be 30% to the pure silicon content of colloidal silica, and 12% to the solution of colloidal silica which is calculated as corresponding to about 2% to the pure silicon content.

TEST EXAMPLE 1

The compositions prepared in Example 1 were used for lauan materials to investigate the impregnation effects. Five cubic lauan materials each having a size of about 1.5 $cm^3$ which had been air-dried and adjusted to the accurate weight were used in an air dried state, and the impregnation was carried out by the vacuum impregnation method with aspirator.

The above-described five wood chips of Sample Nos. 1 to 5 shown in Table 1 below was impregnated for 30 minutes by floating in 250 ml of the solution of colloidal silica, the low molecular weight substance of chitosan and boric acid in the solution in a vacuum, and during the impregnation, the pressure was elevated to an atmospheric pressure twice. After impregnation, the wood chips were dried for 30 minutes in an oven heater at 60° C. A white powder to which colloidal silica had been attached was adhered in a semivitrificated state to the surface of the dried wood chips, and, after removing the powder from the wood chips, each of the chips was weighed. The results obtained are shown in Table 1 below.

TABLE 1

| Sample No. | Weight of Sample (Prior to Impregnation) | Weight of Sample | Assumed Impregnated Amount |
| --- | --- | --- | --- |
| 1 | 3.0 g | 3.7 g | 0.7 g |
| 2 | 3.0 g | 3.8 g | 0.8 g |
| 3 | 3.0 g | 3.6 g | 0.6 g |
| 4 | 3.0 g | 3.5 g | 0.6 g |
| 5 | 3.0 g | 3.8 g | 0.8 g |
|   |   |   | *0.69 g |

TEST EXAMPLE 2

These wood chips treated in Test Example 1 were dried over silica gel in a desiccator for 2 days, and then subjected to a burning test using a gas burner at about 1,200° C. As a result, it was found that the wood chip was carbonated, but no flaming occurred, and colloidal silica which had been crystallized in a vitrified state was found in the carbonized wood.

TEST EXAMPLE 3

The compositions prepared in Example 1 are coated on the surface of a wood chip of Japan cedar, and the resulting wood chip was subjected to the following antimicrobial test against pulp-deteriorating microorganism, *Pullularia pullulans*.

Test Condition: at a humidity of 90% and a temperature of 30° C.

Test Method: Modified Microbial Cell Contact Method

That is, the antimicrobial test was performed using the 12 air-dried wood chips of Japan cedar in plate forms having a size of 3 cm×15 cm×1 cm (thickness). Of these wood chips, three plates (A) coated with the composition of colloidal silica, the low molecular weight substance of chitosan and boric acid; three plates (B) used as control; three plates (c) coated with glucose; and three plates (D) coated with glucose on the coating surface of the composition of colloidal silica, the low molecular weight substance of chitosan and boric acid were allowed to stand for 30 days vertically in a test medium on which the test microorganism had been cultured. The test was conducted at Japan Ohita Prefecture Forestry Experiment Station for a period of from Oct. 3 to Nov. 4, 1993 and the measurements were conducted on the 7th, 14th, 21st and 30th days.

The results obtained are shown in Table 2 below.

TABLE 2

|  |  | 1–7 Days | 8–14 Days | 15–21 Days | 22–30 Days |
| --- | --- | --- | --- | --- | --- |
| Test Sample | A1 | − | − | − | − |
|  | A2 | − | − | − | − |
|  | A3 | − | − | − | − |
| Test Sample | B1 | − | − | + | ++ |
|  | B2 | − | + | + | +++ |
|  | B3 | − | − | ++ | +++ |
| Test Sample | C1 | + | ++ | +++ | +++ |
|  | C2 | + | ++ | +++ | +++ |
|  | C3 | + | ++ | +++ | +++ |
| Test Sample | D1 | − | − | − | − |
|  | D2 | − | − | − | − |
|  | D3 | − | − | − | − |

Note:
−: No black hyphae of the deteriorating microorganism was observed.
+: The deteriorating microorganism was observed.
++: Proliferation of the deteriorating microorganism was propagated.
+++: Proliferation was observed on entire surface of wood chips.

EXAMPLE 3

A 5 wt. % aqueous solution of a low molecular weight substance of chitosan (a mixture of chitosan, chito-oligosaccharide and 2,5-anhydromannose) in 100 ml of pure water having a pH of about 8.5 was prepared, and to 30 ml of the resulting solution were added 250 ml of colloidal silica (a pure $SiO_2$ content, 30.4%; a pure $Na_2O$ content, 0.42 ppm; pH 9.9; viscosity, 5.8 cp) and 20 g of boric acid (a pure $BO_2$ content, 99.5%; pH 4.0). The mixture was stirred overnight to prepare 280 ml of a stable solution having a pH of 7, a viscosity of about 5 cp.

EXAMPLE 4

A low molecular weight substance of chitosan was added to Snowtex S (produced by Nissan Chemical Co., Ltd., a pure $SiO_2$ content, 30.8%; pH 9.9; viscosity, 5 cp), and then boric acid ($BO_2$) was added thereto at various proportions whereby the stability of these compositions was investigated. As a result, a stabilized solution was obtained at a proportion of $SiO_2$ 0.8% and $BO_2$ 8% in 250 ml of water.

TEST EXAMPLE 4

Three test samples of wood chips having an intimately packed grain texture were cut from the same wood material of the Oregon pine. Each of the wood chips had a cut surface area of 500 mm×650 mm and a height of 400 mm, and was dried over silica gel in a reduced pressure desiccator for 168 hours.

The three wood chip samples were then impregnated with 301.18 ml of the aqueous solution prepared in the same manner as in Example 3 for 30 minutes, 60 minutes and 90 minutes (Sample Nos. 1, 2 and 3, respectively) while applying an impregnation pressure of 10 kg per 1 cm$^2$.

After the samples were dried, an impregnated amount was estimated and the results obtained are shown in Table 3. Further, the samples were subjected to a leaching treatment and the fixing ratio of inorganic compounds are calculated. The results are shown in Table 4. As shown in Table 3, the total of the assumed impregnated amounts in Sample Nos. 1 to 3 is 126.18 g which corresponds to 63% impregnation ratio.

TABLE 3

| Sample No. | Weight of Sample (Prior to Impregnation) | Weight of Sample | Assumed Impregnated Amount |
|---|---|---|---|
| 1 | 66.10 g | 107.89 g | 41.80 g |
| 2 | 66.99 g | 111.66 g | 44.67 g |
| 3 | 66.56 g | 106.27 g | 39.71 g |

TABLE 4

| Sample No. | Weight of Sample (Before Impregnation) | Residual Amount of Inorganic Compounds After Leaching | Fixing Ratio of Inorganic Compounds (%) | Treating Time (min) |
|---|---|---|---|---|
| 1 | 66.10 g | 10.52 g | 15.9 | 30 |
| 2 | 66.99 g | 10.52 g | 15.7 | 60 |
| 3 | 66.56 g | 10.52 g | 15.8 | 90 |

EXAMPLE 5

The impregnated pine chip of Sample No. 1 obtained in Test Example 4 was immersed in an acetic acid solution in pure water adjusted to a pH of 4 for about 3 hours, and then the wood chip was immersed in methanol at a pH of 7 for 4 hours, followed by air-drying overnight outside the room.

Separately, the impregnated pine chips of Sample Nos. 2 and 3 obtained in Example 5 were directly immersed in a methanol solution having a pH of 7 for about 2 hours, followed by air-drying overnight outside the room.

Sample No. 1 was found to have finishing color and smell equivalent to or rather more preferred than those of the untreated wood chips, whereas Sample Nos. 2 and 3 were found to have slightly white surfaces.

The crystal structure of colloidal silica in the wood cells of these samples were observed by a scanning type electron microscope. As a result, it was confirmed that the low molecular weight substance of chitosan is present between the crystal structures of the crystallized colloidal silica.

EXAMPLE 6

Fifty g of chitosan (Flonac S, manufactured by Kyowa Tecnos Co., Ltd., molecular weight of not more than 4,000) was dissolved in 1,000 ml of purified water and the pH value was adjusted to 8 to 8.5. Sixty ml of the resulting chitosan solution was added to 1000 ml of colloidal silica (Snowtex C manufactured by Nissan Chemical Co., Ltd.) and the mixture was vigorously stirred for 30 minutes to obtain a transparent and pale brown solution.

To the resulting solution was added 50 g of boric acid (5% of the volume of colloidal silica) slowly with vigorously stirring the mixture. After completion of addition of boric acid, the resulting mixture was further stirred for about 1 hour and the pH value was adjusted to 7.1.

TEST EXAMPLE 5

The composition prepared in Example 6 was used for cedar materials to investigate the impregnation effects. Ten cubic test chips each having a size of 20 mm×20 mm×10 mm which had been air-dried and adjusted to the accurate weight. Five chips in a dry state were allowed to stand under reduced pressure for 2 hours and then impregnated in the composition for 2 hours. Remaining five chips were saturated with water and then impregnated in the composition for 24 hours.

These ten chips were dried at 60° C. for 24 hours in an oven heater and then at 50° C. in a vacuum followed by weighing them.

The chips were further impregnated in purified water for 10 days to leach the substances penetrated into the chips, especially boric acid. This leaching and drying treatment was repeated ten times and the weight of the chips was measured to calculate a leaching ratio. The results are shown in Table 5.

TABLE 5

| | Weight increasing ratio (%) | | Leaching ratio (%) |
|---|---|---|---|
| | after impregnation | after leaching | |
| Impregnation under reduced pressure | 49.41 | 31.94 | 35.4 |
| Impregnation under normal pressure | 66.28 | 45.82 | 30.9 |
| Control | | −10.01 | |

EXAMPLE 7

Mixtures of colloidal silica and a water-soluble low molecular weight chitosan were prepared in the same manner as in Example 6 except for using 1 g of copper (copper (II) chloride • dihydrate, purity: 99.9%), silver (silver nitrate, purity: 99.8%) or titanium (titanium dioxide, purity: 93.0%) in place of boric acid.

TEST EXAMPLE 6

Combustibility of the test chips treated with the composition of the present invention was examined by treating five test chips of cedar materials having a size of 30 mm×50 mm×3 mm in the same manner as in Test Example 5 using the compositions prepared in Examples 6 and 7.

The thus-prepared test chips were exposed to flame (1,000° C.) at a distance of 20 cm from a micro burner. The temperature of the back side of the chips was measured to evaluate combustibility of the chips.

The impregnation effects of the chips are shown in Table 6.

TABLE 6

| | Weight increasing ratio (%) | | | | |
|---|---|---|---|---|---|
| | Boric acid | Copper | Silver | Titanium | Untreated |
| After impreg- | 24.12 | 17.74 | 21.42 | 22.59 | −1.87 |

TABLE 6-continued

| | Weight increasing ratio (%) | | | | |
|---|---|---|---|---|---|
| | Boric acid | Copper | Silver | Titanium | Untreated |
| nation After leaching | 18.47 | 15.38 | 19.93 | 20.72 | −2.92 |

Figure 1:
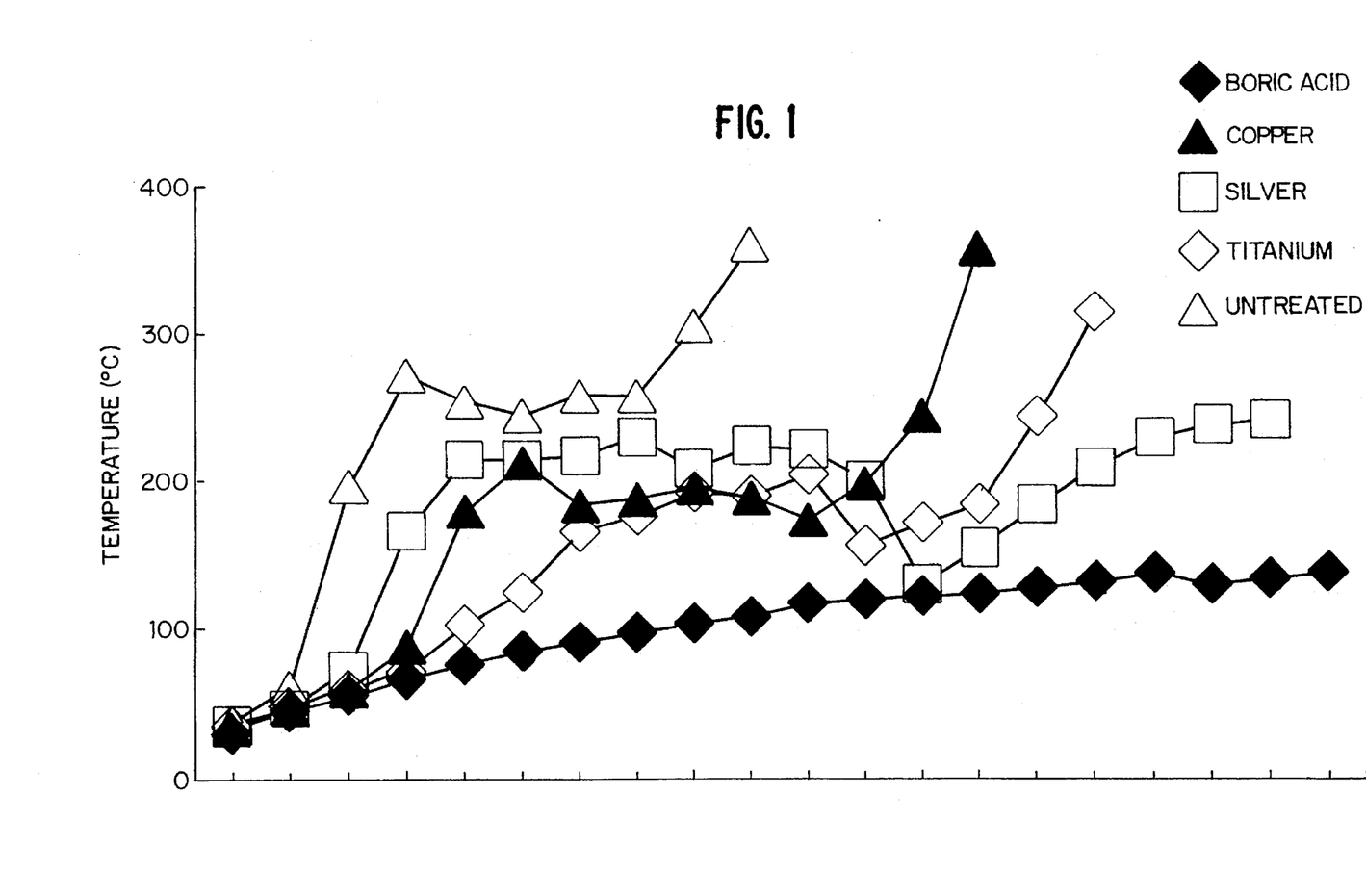
FIG. 1 shows the results of the combustion test before the leaching treatment.
Figure 2:
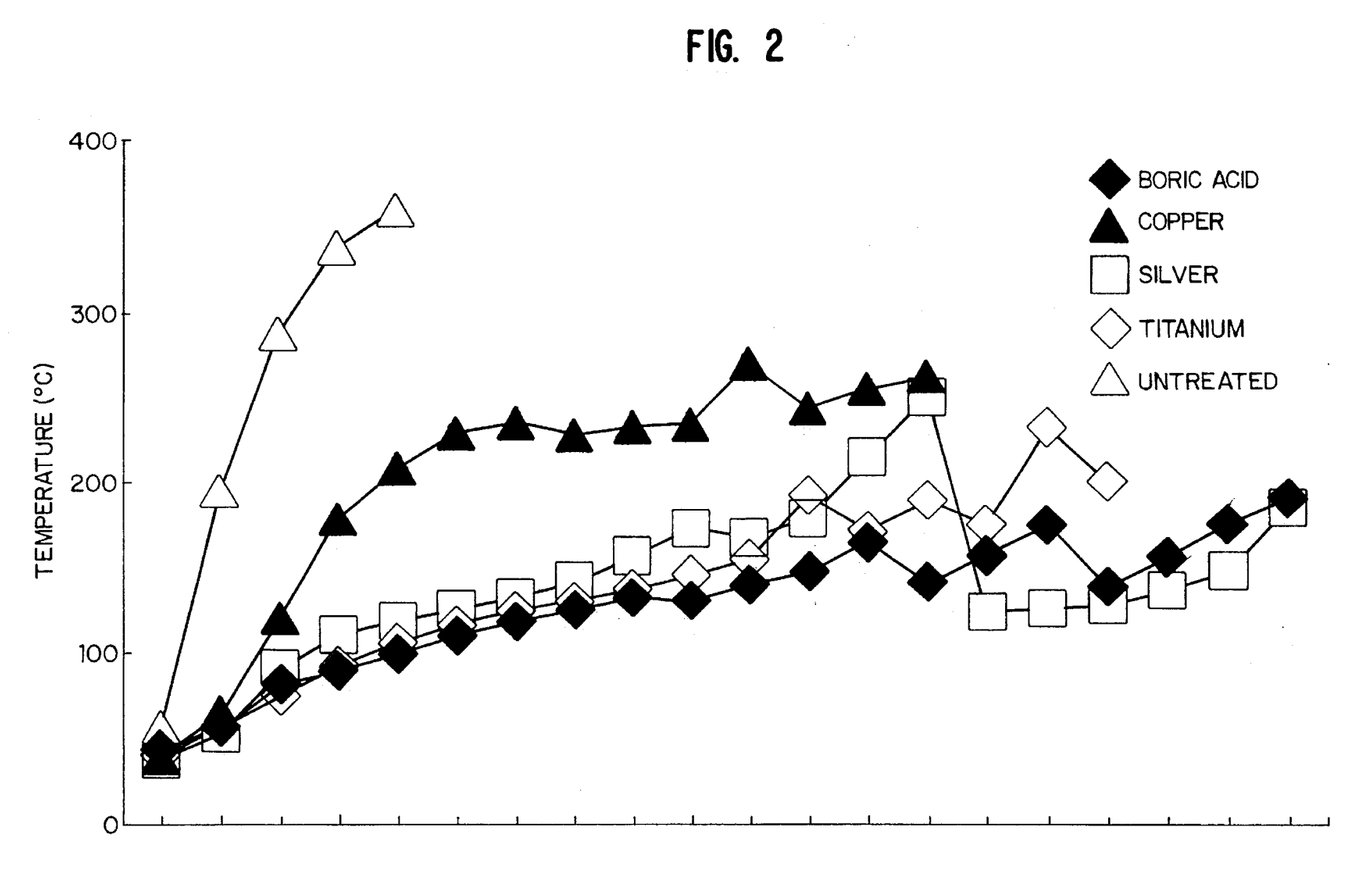
FIG. 2 shows the results of the combustion test after the leaching treatment.

The results of combustibility of the chips are shown in FIG. 1 and FIG. 2, which illustrate combustibility before and after the leaching treatment, respectively.

TEST EXAMPLE 7

Figure 3:
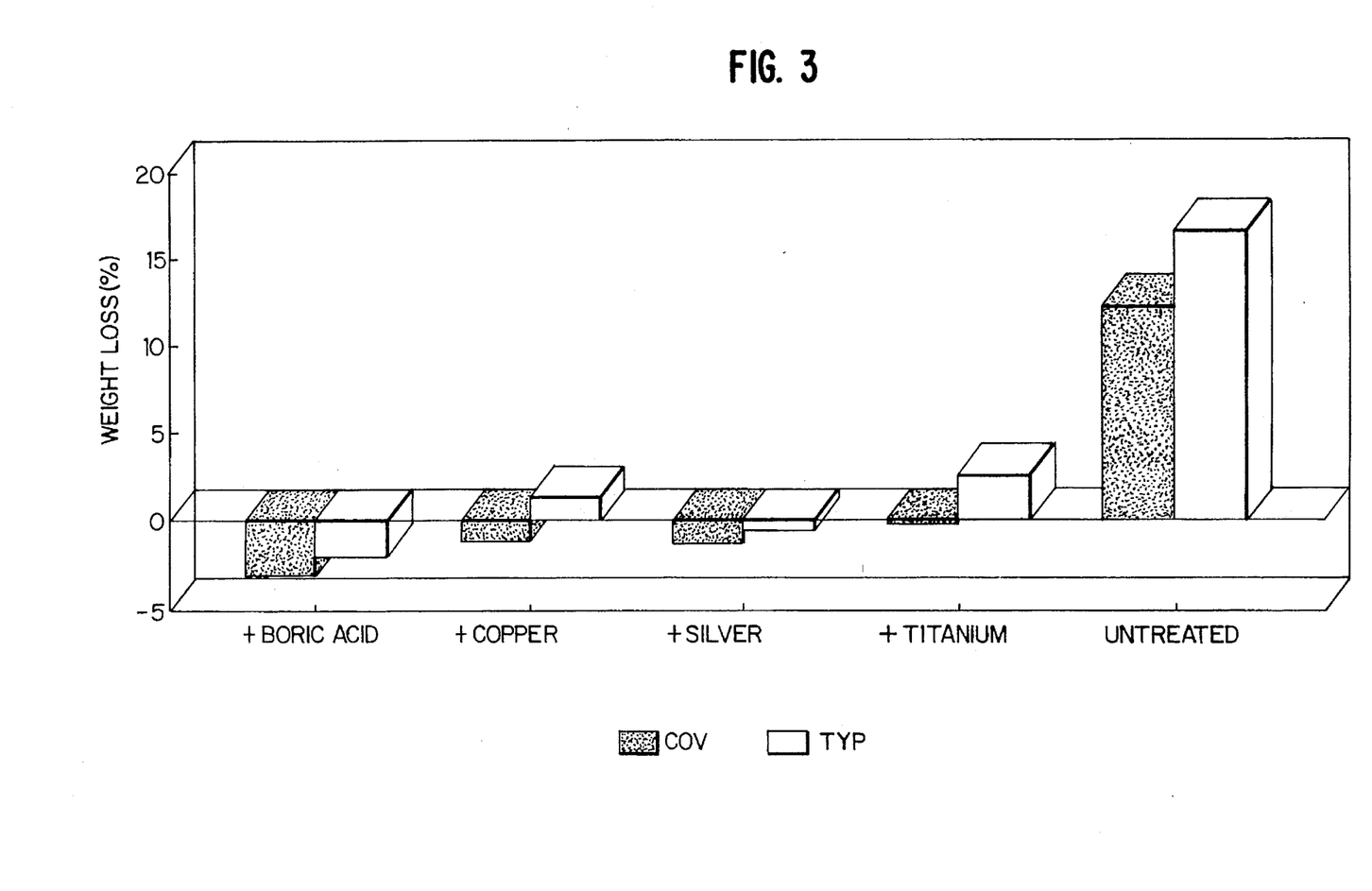
FIG. 3 shows the results of the test on the antiputrefactive effect before the leaching treatment.
Figure 4:
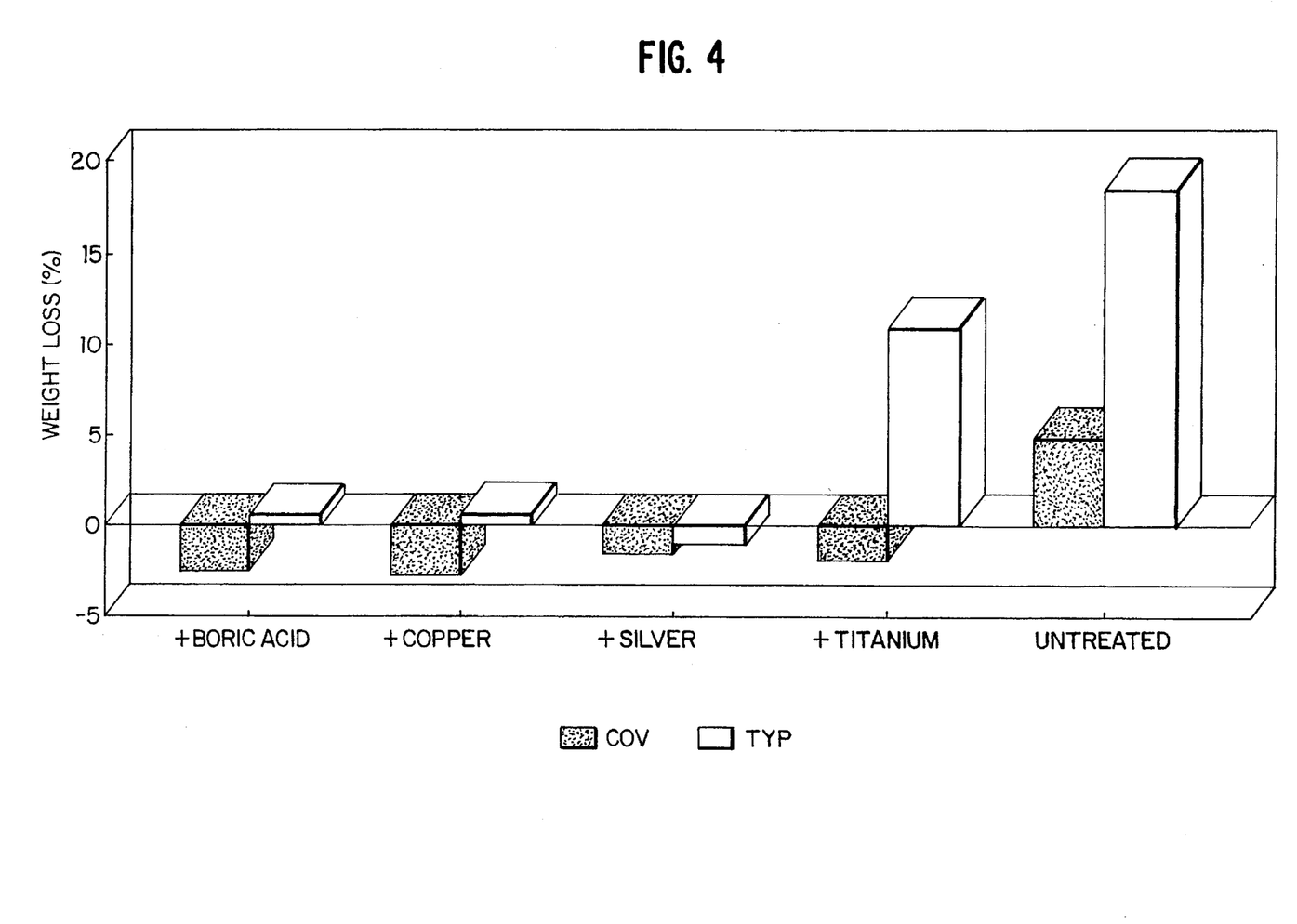
FIG. 4 shows the results of the test on the antiputrefactive effect after the leaching treatment.

An antiputrefactive effect of the composition of the present invention was examined using Coliolus and Tyromyces as test strains. These strains were each cultured in a medium using an incubator. The test chips were put into the culture medium and allowed to stand for six months. Then, the weight loss ratio was determined and evaluated as an index of the antiputrefactive effect. The results are shown in FIG. 3 and FIG. 4.

While the invention has been described in detail and with reference to specific embodiments thereof, it will be apparent to one skilled in the art that various changes and modifications can be made therein without departing from the spirit and scope thereof.

What is claimed is:

1. A wood modifier composition comprising a mixture of a water-soluble chitosan having a molecular weight ranging from 320 to 48,000, and colloidal silica wherein said colloidal silica is present in the composition in an amount of from 15 to 300 parts by weight per part by weight of said chitosan.

2. The wood modifier composition as claimed in claim 1, wherein said composition further comprises one or more compounds selected from the group consisting of metal compounds, silicon compounds, germanium compounds, arsenic compounds, boron compounds and carbon compounds.

3. The wood modifier composition as claimed in claim 2, wherein said metal compounds are selected from the group consisting of copper compounds, silver compounds, antimony compounds, bismuth compounds and titanium compounds and said boron compound is boric acid.

4. The wood modifier composition as claimed in claim 1, wherein said colloidal silica is present in the composition in an amount of from 50 to 150 parts by weight per part by weight of said chitosan.

5. The wood modifier composition as claimed in claim 3, wherein said colloidal silica and boric acid are present in the composition in an amount of from 15 to 300 parts by weight and 5 to 50 parts by weight, respectively, per part by weight of said chitosan.

6. The wood modifier composition as claimed in claim 3, wherein said colloidal silica and metal compounds are present in the composition in an amount of from 15 to 300 parts by weight and 0.01 to 10 parts by weight, respectively, per part by weight of said chitosan.

7. The wood modifier composition as claimed in claim 1, wherein the composition has a pH value ranging from pH 5 to 12.

8. The wood modifier composition as claimed in claim 1, wherein the composition has a pH value ranging from pH 6 to 10.

9. The wood modifier composition as claimed in claim 2, wherein said boron compounds are selected from the group consisting of boric acid, calcium borate, borax and borosilicate.

10. The wood modifier composition as claimed in claim 2, wherein said metal compounds are selected from the group consisting of copper compounds, silver compounds, titanium compounds, chromium compounds antimony compounds, bismuth compounds and iron compounds.

11. A method of improving the quality of wood materials which comprises impregnating wood materials in a composition comprising a mixture of a water-soluble chitosan having a molecular weight ranging from 320 to 48,000, and colloidal silica wherein said colloidal silica is present in the composition in an amount of from 15 to 300 parts by weight per part by weight of said chitosan.

12. The method as claimed in claim 11, wherein said composition further comprises one or more compounds selected from the group consisting of metal compounds, silicon compounds, germanium compounds, arsenic compounds, boron compounds, and carbon compounds.

13. The method as claimed in claim 12, wherein said metal compounds are selected from the group consisting of copper compounds, silver compounds, titanium compounds, antimony compounds and bismuth compounds and said boron compound is boric acid.

14. The method as claimed in claim 11, wherein said colloidal silica is present in the composition in an amount of from 50 to 150 parts by weight per part by weight of said chitosan.

15. The method as claimed in claim 13, wherein said colloidal silica and boric acid are present in the composition in an amount of from 15 to 300 parts by weight and 5 to 50 parts by weight, respectively, per part by weight of said chitosan.

16. The method as claimed in claim 13, wherein said colloidal silica and metal compounds are present in the composition in an amount of from 15 to 300 parts by weight and 0.01 to 10 parts by weight, respectively, per part by weight of said chitosan.

17. The method as claimed in claim 11, wherein said composition has a pH value that ranges from pH 5 to 12.

18. The method as claimed in claim 11, wherein said composition has a pH value that ranges from pH 6 to 10.

19. The method according to claim 12, wherein said boron compounds are selected from the group consisting of boric acid, calcium borate, borax and borosilicate.

20. The method according to claim 12, wherein said metal compounds are selected from the group consisting of copper compounds, silver compounds, titanium compounds, chromium compounds antimony compounds, bismuth compounds, and iron compounds.

\* \* \* \* \*